United States Patent [19]

von Soiron et al.

[11] 4,159,020

[45] Jun. 26, 1979

[54] MASSAGE BELT FOR WEARING IN THE REGION OF THE HUMAN LUMBAR VERTEBRAL COLUMN

[76] Inventors: Ferdinand F. von Soiron; Gertrud F. von Soiron nee Behnke, both of Wullnerstr. 145, 5000 Cologne 41, Fed. Rep. of Germany

[21] Appl. No.: 814,910

[22] Filed: Jul. 12, 1977

[30] Foreign Application Priority Data

Mar. 15, 1977 [DE] Fed. Rep. of Germany ....... 2711170

[51] Int. Cl.² .......................... A61H 1/00; A61F 5/02; A61F 5/26
[52] U.S. Cl. ..................................... 128/24 R; 128/78; 128/99
[58] Field of Search ...................... 128/95, 96, 105, 78, 128/24 R, 60, 103

[56] References Cited

U.S. PATENT DOCUMENTS

| | | | |
|---|---|---|---|
| 968,728 | 8/1910 | Ballou | 128/105 |
| 1,012,101 | 12/1911 | Roach | 128/105 |
| 1,063,009 | 5/1913 | Cluthe | 128/106 |
| 1,542,717 | 6/1925 | Pease | 128/106 |
| 2,454,833 | 11/1948 | Pfahl | 128/106 |
| 2,733,712 | 2/1956 | Wuesthoff | 128/78 |
| 3,171,409 | 3/1965 | Cetrone | 128/99 |
| 3,605,731 | 9/1971 | Tigges | 128/95 |

FOREIGN PATENT DOCUMENTS 398048 3/1909 France ......................................... 128/95

*Primary Examiner*—Lawrence W. Trapp
*Attorney, Agent, or Firm*—Neil F. Markva

[57] ABSTRACT

A massage belt comprises a belt member having a pair of support elements laterally spaced from each other at the same distance from the middle of the belt member. The support elements are disposed on a carrier and one support element is caused to be flexible with respect to the belt member and further caused to be resiliently resetting with respect to the other support element. The massage belt is worn in the region of the human lumbar vertebral column. The support member is torsionally flexible with respect to the belt member. A connecting strap is disposed between portions of the carrier means holding the support elements. The connecting strap is torsionally elastic and resiliently retractable. Various shapes and mounting dispositions are used for the support elements laterally spaced from each other on said belt member.

22 Claims, 8 Drawing Figures

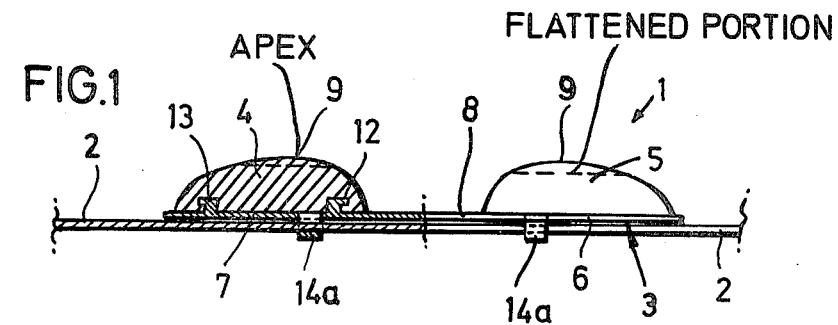
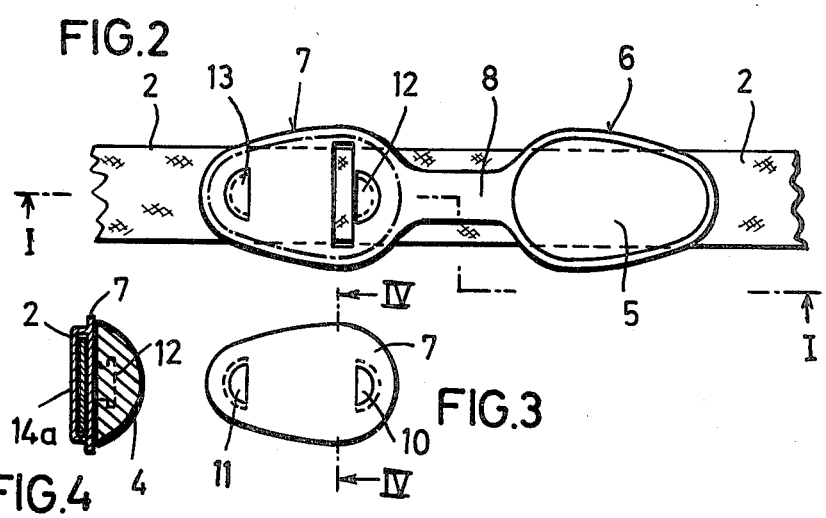
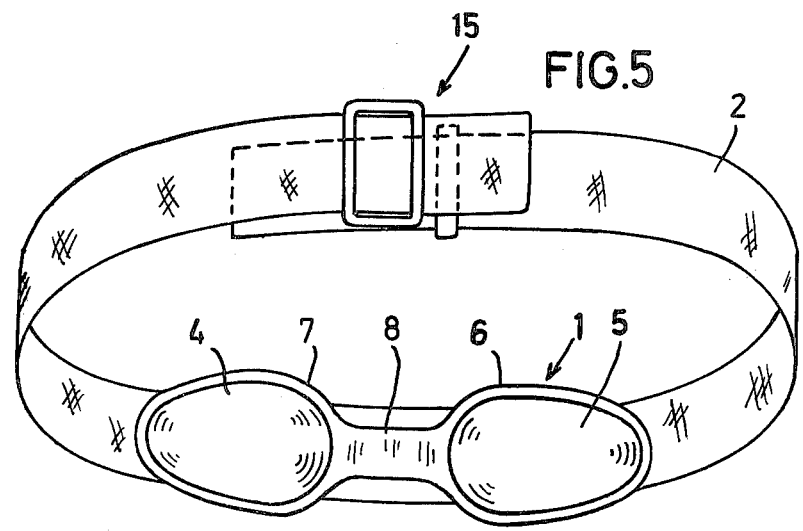

MASSAGE BELT FOR WEARING IN THE REGION OF THE HUMAN LUMBAR VERTEBRAL COLUMN

BACKGROUND OF THE INVENTION

This invention relates to a massage belt for wearing in the region of the human lumbar vertebral column. The massage belt includes a strap having a pair of support elements or pads that are laterally displaced with respect to each other.

There are many known bindings and support arrangements to be worn in the region of the human lumbar vertebral column. Bodice or corset-like bindings are used and intended for direct support of the lumbar vertebral column or individual lumbar vertebral column sections. Support elements frequently extend in the longitudinal direction of the lumbar vertebral column and rest directly against the column for the purpose of fitting in place. Bodices or corsets frequently reach upwardly and downwardly far beyond the width of the belt member on which they are mounted. Consequently, the bodices or corsets reach beyond the waist of the wearer in order to keep the body firmly bound up within the lumbar region.

There are further known corset devices which can be firmly tightened about the trunk for supporting or correcting the human lumbar vertebral column. These prior art devices bear at their innersides symmetrically on both flanks close to the lumbar vertebral column support members coming to rest against the back. Two support members located at the same level are interconnected at any given time by a bridging element. Thus, a plurality of briding elements are provided one below the other. The vertical spacing of these briding elements with respect to each other, at any particular time, is about equal to the thickness of the ligamentary disks. In this case, the bridging elements are pivotally attached to their upper parts to a central vertical bar. Such a prior art belt has a considerable depth and reaches over a plurality of vertebrae of the lumbar vertebral column. Stiffening rods are provided in the comparatively broad belt and a reinforcing strap is attached to the lower edge around the outside of the belt.

A disadvantage of this type of prior art belt is that the mobility of the muscular system is more or less restricted. They support the trunk at the level of the lumbar vertebral column and therewith render mobility of the muscular system more or less sluggish. With belts in the form of a bodice or corset, the lumbar vertebral column is immobilized. The back stretching muscular system and the mobility of the lumbar vertebrae pertaining thereto is wholly or partly restricted in its operational sequences.

Further, there are prior art belts which have only one pair of support elements or pads that are arranged to both sides of and at the same distance from the middle of the belt. The support elements are directly mounted on the flexible belt member. With such a pior art belt, a certain massaging effect can be achieved to prevent spasms in the braced back muscular system in the region of the human lumbar vertebral column. However, as the support elements accompany the comparatively flexible belt, the action on the back-stretching muscular system is not always adequate for relaxation of the latter.

SUMMARY OF THE INVENTION

As described and disclosed herein, a massage belt is provided for wearing in the region of the human lumbar vertebral column, in which collaboration of the back muscular system to relax the latter to a very large extent is stimulated and a pronounced massage action on the cramped back muscular system is exercised while wearing the belt. The support elements are disposed at the same distance from the middle of the belt with respect to each other and arranged on a common support. The belt member consits of elastomeric material. One support element is arranged on the common support to be flexible with respect to the belt and resiliently resetting with respect to the other support element. In a specific embodiment, the said one support element is torsionally flexible with respect to the massage belt.

The massage belt made in accordance with this invention, enables the exercise of an action principle with a point of application on the back muscular system specific to the trunk. That is, exercise of the long back-stretching muscles may be made to the left and right of the spinal column at about the level of the fifth lumbar vertebrae, at which position occurs the majority of all acute and chronic lumbar cartilaginous injuries. Such a massage potential provides relaxation of both the acutely-braced and the chronically-braced muscular system. The torsionally flexible middle piece between the support or bearing elements at the support enables the exercise of a continuous automatic massage while wearing the massage belt. By this mechanism, the muscular system retains its freedom of action and is activated up to a normal tone.

The flexible, resilient and resetting mounting of the support or bearing elements with respect to each other provides a massaging, pressing or squeezing action on the aforementioned positions of the back-stretching muscles. This respective movement of the elements with respect to each other provides for the relaxation and release of tension in the cramped back muscular system and at the same time leads to a more vigorous irrigation strengthening of the back muscular system. The mounting retains its full freedom of movement while the belt is being worn. Only through such a mounting is a prerequisite for the strengthening of the status and recovery of the flexibility of the spinal column fulfilled. Further, the pressing or squeezing massage relaxes the back-stretching muscles and also strengthens the latter to the normal tone whereby the danger of locking of the lumbar section is excluded. The projective stiffened lumbar spinal column section is freed and mobilized as the muscular system regains physiological freedom of action. The massage belt made in accordance with this invention goes along with the lumbar spinal column sections on movement of the trunk and also the support elements carry out their resilient resetting arrangement to each other thereby providing an optimum in additional massage and squeezing or pressing. This action leads to loosening and relaxing of the cramped muscular system so that it can again exercise its physiological supporting function. This is indispensable for elimination of pains resulting, for example, through ligament disk damages.

The torsionally elastic characteristics and the resiliently retractable application of one support element with respect to the other support element may be achieved in various ways. A connecting strap is placed between the parts of the carrier holding the support elements in one embodiment. The connecting strap is formed to be torsionally elastic and at the same time resiliently retractable. Such a connecting strap may be constructed in various ways. The strap may be given a smaller width than the support elements. Moreover, the connecting strap may be kept thinner with respect to the thickness of the material than the adjacent carrier portions. Thus, the common carrier may consist of inherently resilient material. It is further possible that the connecting strap may have a higher elasticity than those of the carrier portions. It is necessary that the connecting strap be flexible and, at the same time, resiliently retractable. Instead of using a separate carrier for the support elements, the elastic support elements may also be integrally formed with the torsionally elastic and resiliently retractable connecting strap.

A further embodiment may advantageously include, support elements fastened to a strap-shaped carrier kept substantially uniform in width over its length and retractable and elastic over its length. With this, the carrier strap as a whole is capable, in itself, of twisting to a greater or lesser extent.

A further important feature of this invention is the distance apart at which the operative reaches of the support elements are disposed with respect to each other. Considering the most varied human types, it has been shown that the distance apart of the middle zones of the two back stretch muscular systems extending at the sides of the vertebral column, varies only between about 5 cm and at most about 7 cm. Accordingly, the support elements are disposed at both sides of the connecting strap with their centers of pressure and the distance apart in the range from about 5 cm and 7 cm. In a specific embodiment, the distance is limited to 6 cm. Thus, it is guaranteed that the support elements can bear on each occasion upon the middle zone of the back stretch muscular system.

Advantageously, the support elements are cupola-shaped at their operative reaches and slope off all around from this cuploa shape. The sloping off in the direction away from the middle of the belt is less than the sloping off towards the middle of the belt or the other directions. Thus, the support elements may have a somewhat tear-shaped form in plan view. A somewhat elongate form of the support elements assist the massaging action on the back muscular system. This is true even where the trunk is bent or straight or the upper trunk carries out a certain rotary movement with respect to the lower trunk or the legs. The uppermost part of the cupola surfaces of the support elements may be flattened. Such a flattening should be kept in a diameter not greater than about 15 to 20 mm.

The elasticity of the support elements also contributes significantly to the massaging action. In a specific embodiment, the support elements consist of rubber elastic material having a Shore hardness in the range of about 10 to 18 in value.

The elastic support elements may be attached to the carrier in several different ways. The elements may be fixed to the common carrier by adhesion such as by gumming or adhesive material. A mechanical locking mechanism may be used to releasably fix the elements to the common carrier. Such a mechanical locking would include button-shaped or hook-shaped parts, which are engaged by the support elements by means of undercut recesses. With the detachably fixed mechanical locking mechanism, the support elements may be easily replaced or interchanged.

The belt member may be guided in slots located in the carrier so that the set of support elements can be pushed along the belt member in a desired manner for adjustment on fitting the belt member to the trunk. Slots in one embodiment are disposed at the end of the carrier. A specific embodiment of the carrier consists of a stiff and, at the same time, elastically resilient plastics material.

BRIEF DESCRIPTION OF DRAWINGS

Other objects of this invention will appear in the following description and appended claims, reference being made to the accompanying drawings forming a part of the specification wherein like reference characters designate corresponding parts in the several views.

FIG. 1 is a fragmentary diagrammatic view along line I—I of FIG. 2;

FIG. 2 is a fragmentary top-plan view of the massage belt of FIG. 1;

FIG. 3 is a back elevational view of a support element on the massage belt made in accordance with this invention;

FIG. 4 is a cross-sectional view along line IV—IV of FIG. 3;

FIG. 5 is a diagrammatic perspective view of a massage belt made in accordance with this invention;

DESCRIPTION OF SPECIFIC EMBODIMENTS

Figure 6:
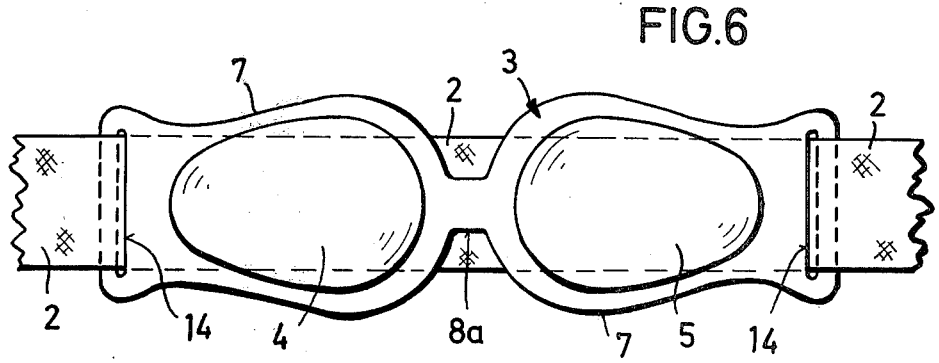
FIG. 6 is a fragmentary top-plan view of another embodiment of a massage belt made in accordance with this invention.

The massage belt, generally designated 1, is to be worn in the region of the human lumbar vertebral column and includes a belt member 2 having a carrier, generally designated 3, which includes support elements or pads 4 and 5. The support elements 4 and 5 are laterally displaced with respect to each other at a predetermined distance apart. Advantageously, the elements 4 and 5 are at the same distance from the transverse center of the belt member 2 and are composed of a rubber elastic material of suitable quality. Support elements 4 and 5 are fixedly secured to carrier portions 6 and 7 of the carrier 3.

Element or strap 8 connects carrier portions 6 and 7 and is formed or shaped to be torsionally elastic, inherently resilient and, at the same time, resiliently retractable in itself. That is, connecting strap 8 has a width that is considerably less than the width of carrier portions 6 and 7 or support elements 4 and 5 while consisting of inherently resilient material. Furthermore, connecting strap 8 may be kept thinner in cross-sectional thickness than carrier portions 6 and 7. The material of strap 8 may have a higher elasticity than the material used in carrier portions 6 and 7, even though they all combine together to form a single carrier 3. Any of these structural features may be used individually or in combination with each other.

When the massage belt 1 is worn within the region of the human lumbar vertebral column, the support elements 4 and 5 exercise an independent and very efficient massaging action on the back muscular system passing close to the vertebral column. Massaging action is effected through the torsionally elastic shaping of the connecting strap 8 and occurs when the person is walking or producing other movement of the trunk or body. The zone of the vertebral column itself is kept clear of contact by the support elements 4 and 5 because they are laterally disposed with respect to each other. Connecting strap 8 may be curved inwardly or outwardly if desired.

In one specific embodiment, supporting elements 4 and 5 are formed of rubber elastic material and have a predetermined Shore hardness within the range of about 10 to 18 and more specifically, within the range of 12 to 16. Thus, the massaging action striven for is fully effective but will not lead to compression. Elements 4 and 5 have an operative reach 9 which is somewhat cuploa-shaped or dome-shaped in form and slopes off all around from the cuploa or dome. The nature of the sloping off is lesser in the direction away from the middle of the belt 1 than either toward the belt 1 or to the sides of the respective support element.

In a further embodiment, the uppermost portion of the support elements 4 and 5 may be flattened. However, such a flattening should not exceed about 15 to 20 mm in diameter. The depth of the support elements may be about 20 mm and the length thereof be within the range of about 75 to 90 mm, and if necessary, depending upon the circumstances, up to about twice that. Reaches 9 of support elements 4 and 5, operative in the first place, are provided at a distance about from the apex of one to the apex of another of about 5 cm to 7 cm. In a specific embodiment, the distance apart is about 6 cm whereby the massage belt 1 is suitable for all sizes and types of trunk or body. Support elements 4 and 5 where extending along the longitudinal axis of belt member 2 should not overlap or stand out only slightly from the width of the belt member 2.

Adhesive bonding such as glue may be used to fasten support elements 4 and 5 to carrier 3. Alternatively, elements 4 and 5 are releasably secured to the common carrier 3 with a mechanical locking mechanism. The locking mechanism may include button-shaped or hook-shaped attachments 12 and 13 located on carrier portions 6 and 7. Undercut recesses 10 and 11 engage attachments 12 and 13 thereby fixedly holding support elements or pads 4 and 5 onto carrier portions 6 and 7. In this embodiment, elements 4 and 5 may be easily exchanged for other support elements as desired.

Figure 7:
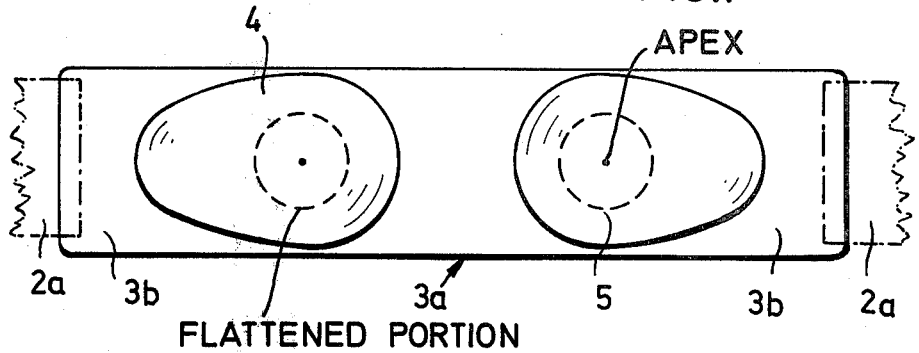
FIG. 7 is a fragmentary plan view of a further embodiment of a massage belt made in accordance with this invention.

Another feature of the invention requires carrier 3 to be slidably disposed along belt member 2. Carrier 3 includes slots 14 or loops 14a through which belt member 2 is guided. Slots 14 or loops 14a are disposed at the end portions of the carrier 3 as shown in FIG. 6. In this way, the end edges of carrier 3 are secured against contact with the skin. The thickness of the carrier material is in the range of from about 0.5 to 1.5 mm. The embodiment of FIG. 7 shows a carrier 3a having a substantially uniform width over its entire length. The belt shaped carrier 3a is inherently capable of twisting and at the same time is elastically retractable. Belt portions 2a end at the carrier end parts 3b and are secured thereto.

Belt member 2 is generally composed of elastic material and has an elongation of about 40 to 50%. A specific embodiment of belt member 2 is composed of a textile-rubber web having rounded edges. Generally, the width of belt member 2 is between about 35 and 50 mm. The ends of belt member 2 may be kept together by a buckle 15 as shown in FIG. 5. Other closure elements may also be used to adjust belt member 2 to correspond to the trunk girth.

Quick and reliable relaxation of the braced back muscular system in the region of the lumbar vertebral column is possible with the massage belt of this invention having several inventive features. These features include the torsionally elastic and, at the same time, resiliently retractable connecting portion of the carrier located between the support elements. Another feature is the massage favoring cupola-shaped support elements. Another feature is the comparatively light application of the belt member being disposed around the human trunk in the region of the lumbar vertebral column.

Figure 8:
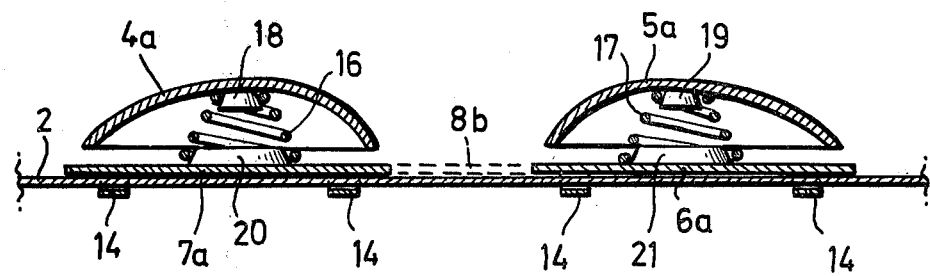
FIG. 8 is a fragmentary sectional view of a still further embodiment of a massage belt made in accordance with this invention.

In the embodiment of FIG. 8, each support element 4a and 4b is individually resiliently retractable and torsionally elastically disposed on the carrier portion 7a and 6a, respectively. Each element 4a and 4b is supported and held by at least one coil spring 16 and 17, respectively. Thus, elements 4a and 4b can effect rocking motions in all directions and be restored again to its normal position through the action of springs 16 and 17. Each support element 4a and 5a is supported as is a universal balance. In this way, the resiliently retractable application along with corresponding torsional elasticity of the pertaining support elements is effected.

Several springs may be used on one and the same support element in place of the single springs 16 and 17 as shown. Support elements 4a and 4b are advantageously disk-shaped and consist of suitable material of more or less stiff or a stiff resilient nature. Attachments 18 and 19 are disposed on the respective inner surfaces of support elements 4a and 5a and engage the respective springs 16 and 17. Springs 16 and 17 are supported on the respective carrier portions 7a and 6a and may be fixedly held in any suitable manner. Carrier portions 7a and 6a have attachments 20 and 21 over which springs 16 and 17 correspondingly engage.

Carrier portions 6a and 7a may be independent members having belt member 2 guided through loops 14 disposed thereon. Alternatively, carrier portions 6a and 6b may be interconnected by a connecting strap 8b formed to be torsionally elastic and resiliently retractable in conformity with the embodiments of FIGS. 1 through 4. In this latter instance, a double mounting of support elements 6a and 7a is effected with regard to the torsional elastic and resiliently retractable arrangement thereof. That is, the benefit of the mounting including the springs 16 and 17 is additive to the effect of the common connecting strap 8b. Consequently, the massage action for relaxing the braced back muscular system is further intensified.

While the massage belt for wearing in the region of the human lumbar vertebral column has been shown and described in detail, it is obvious that this invention is not to be considered as being limited to the exact form disclosed, and that changes in detail and construction may be made therein within the scope of the invention, without departing from the spirit thereof.

Having thus set forth and disclosed the nature of this invention, what is claimed is:

1. A massage belt for wearing in the region of the human lumbar vertebral column, comprising:
  (a) a belt member having a pair of support elements laterally spaced from one another at the same distance from the middle of the belt member,
  (b) each said support element being disposed on a different portion of a carrier means, and (c) said carrier means including a torsionally elastic portion which connects the different portions carrying the support elements, (d) said torsionally elastic portion being effective to torsionally reset one support element with respect to the other support element during use by the wearer.

2. A massage belt as defined in claim 1 wherein said torsionally elastic portion includes a connecting strap extending between the portions of the carrier means holding the support elements, said connecting strap being torsionally elastic and at the same time resiliently retractable.

3. A massage belt as defined in claim 2 wherein the connecting strap is of lesser width than the support elements.

4. A massage belt as defined in claim 2 wherein the connecting strap is composed of material having a higher elasticity than the material forming said carrier portions holding the support elements.

5. A massage belt as defined in claim 2 wherein the support elements are formed to be dome-shaped internally or externally.

6. A massage belt as defined in claim 1 wherein the support elements are fastened to a strap-shaped carrier kept substantially uniform in width and retractably elastic over its length, said strap-shaped carrier being composed of a material that is capable of twisting to provide said torsionally elastic portion between the support elements.

7. A massage belt as defined in claim 1 wherein said support elements have respective operative reaches arranged at a distance apart of about 5 to 7 cm.

8. A massage belt as defined in claim 7 wherein said support elements have respective operative reaches arranged at a distance apart of about 6 cm.

9. A massage belt as defined in claim 1 wherein the support elements are cupola-shaped or dome-shaped in form and slope off all around from this cupola or dome, the nature of the sloping-off being lesser in the direction away from the middle of the belt than in the other directions.

10. A massage belt as defined in claim 9 wherein the uppermost part of the cupola or dome surface is flattened, and the flattened-off surface is about 15 to 20 mm in diameter.

11. A massage belt as defined in claim 1 wherein the support elements are tear-shaped in plan.

12. A massage belt as defined in claim 1 wherein the elastic support elements have a Shore hardness of about 10 to 18.

13. A massage belt as defined in claim 1 wherein the elastic support elements are releasably arranged on the carrier means.

14. A massage belt as defined in claim 1 wherein the elastic support elements are releasably disposed on said carrier with at least one conical spring therebetween, said spring being mechanically locked in place.

15. A massage belt as defined in claim 1 wherein the support elements are fastened to a strap-shaped carrier kept substantially uniform in width and retractably elastic over its length, said elastic support elements having undercut recesses and being fixed on button-shaped or hook-shaped attachments on the carrier means.

16. A massage belt for wearing in the region of the human lumbar vertabral column, comprising:

(a) a belt member having a pair of support elements laterally spaced from one another at the same distance from the middle of the belt member, (b) said support elements being disposed on a carrier means, and (c) means causing one support element to be flexible with respect to the belt member and resiliently resetting with respect to the other support element, (d) the belt member is guided in slots or loops of the carrier which carrier is movable along the belt member, (e) the slots or loops holding the belt member being arranged at the end portions of the carrier.

17. A massage belt as defined in claim 1 wherein said carrier means has end portions and ends of the belt member start from the end portions of the carrier means.

18. A massage belt as defined in claim 1 wherein the carrier means consists of stiff, elastically-resilient plastics material.

19. A massage belt as defined in claim 1 wherein said torsionally elastic portion includes a connecting strap extending between the portions of the carrier means holding the support elements, said connecting strap being torsionally elastic and at the same time resiliently retractable, the elastic support elements being integrally formed with the torsionally-elastic and resiliently-retractable connecting strap.

20. A massage belt as defined in claim 1 wherein said carrier means comprises a carrier plate including a connecting strap extending between the portions of the carrier plate holding the support elements, said connecting strap constituting said torsionally elastic portion.

21. A massage belt as defined in claim 20 wherein the connecting strap is of lesser width than said support elements.

22. A massage belt as defined in claim 20 wherein the connecting strap is composed of material having a higher elasticity than the material of the carrier plate portions holding the support elements.

* * * * *